United States Patent
Kraenzle (10) Patent No.: US 6,203,322 B1
(45) Date of Patent: Mar. 20, 2001

(54) DENTAL PROPHYLAXIS ANGLE

(76) Inventor: David Kraenzle, 511 Sarah La., St. Louis, MO (US) 63141

( * ) Notice: Subject to any disclaimer, the term of this patent is extended or adjusted under 35 U.S.C. 154(b) by 0 days.

(21) Appl. No.: 09/292,218

(22) Filed: Apr. 15, 1999

(51) Int. Cl.$^7$ .................................................... A61C 3/06
(52) U.S. Cl. ........................................... 433/125; 433/126
(58) Field of Search ................................... 433/125, 126, 433/127, 114, 116

(56) References Cited

U.S. PATENT DOCUMENTS

| Re. 34,997 | * | 7/1995 | Kraenzle | 433/126 |
|---|---|---|---|---|
| 144,744 | | 11/1873 | Cottrell . | |
| 170,178 | | 11/1875 | Locke . | |
| 186,471 | | 1/1877 | Gilbert . | |
| 186,504 | | 1/1877 | Starr . | |
| 207,079 | | 8/1878 | Starr . | |
| 301,936 | | 7/1884 | Swasey . | |
| 307,686 | | 11/1884 | Starr . | |
| 319,110 | | 6/1885 | Miller . | |
| 341,925 | | 5/1886 | Lemassena . | |
| 361,806 | | 4/1887 | Ballard . | |
| 362,808 | | 5/1887 | Wood . | |
| 387,581 | | 8/1888 | Custer . | |
| 391,302 | | 10/1888 | Deane . | |
| 409,837 | | 8/1889 | Hardie . | |
| 425,897 | | 4/1890 | Morrison . | |
| 426,994 | | 4/1890 | Halsey . | |
| 441,524 | | 11/1890 | Whitcomb . | |
| 456,208 | | 7/1891 | Schycker . | |
| 462,896 | | 11/1891 | Eddy . | |
| 471,887 | | 3/1892 | Park . | |
| 485,010 | | 10/1892 | Jones . | |
| 517,248 | | 3/1894 | Stanbrough . | |
| 517,249 | | 3/1894 | Stanbrough . | |
| 645,345 | | 3/1900 | Young . | |
| 656,124 | | 8/1900 | Kinnison . | |
| 682,308 | | 9/1901 | Young . | |
| 689,596 | | 12/1901 | Platt . | |
| 750,639 | | 1/1904 | Graft . | |
| 781,587 | | 1/1905 | Blake . | |
| 870,825 | | 11/1907 | Hardy . | |
| 899,626 | | 9/1908 | Schultz . | |
| 1,112,565 | | 10/1914 | Schultz . | |
| 1,179,216 | | 4/1916 | Ragatz . | |
| 1,238,883 | | 9/1917 | Burlew . | |
| 1,277,020 | | 8/1918 | Young . | |
| 1,292,632 | | 1/1919 | Nemmers . | |
| 1,294,423 | | 2/1919 | Davis . | |
| 1,299,137 | | 4/1919 | Davis . | |
| 1,332,744 | | 3/1920 | Nelson . | |
| 1,333,809 | | 3/1920 | Laurer et al. . | |
| 1,335,825 | | 4/1920 | Ellerbeck . | |
| 1,342,968 | | 6/1920 | Moolten . | |
| 1,354,139 | | 9/1920 | Shaw . | |
| 1,356,352 | | 10/1920 | Gonzalez . | |
| 1,368,195 | | 2/1921 | Pearl . | |
| 1,379,445 | | 5/1921 | Gonzalez . | |
| 1,379,880 | | 5/1921 | Seaborn . | |
| 1,380,717 | | 6/1921 | Herman . | |
| 1,381,697 | | 6/1921 | Bishop . | |
| 1,405,249 | | 6/1922 | Young . | |
| 1,406,263 | | 2/1922 | Kühn . | |
| 1,417,584 | | 5/1922 | Stempel, Jr. . | |
| 1,427,503 | | 8/1922 | Wake . | |
| 1,458,293 | | 6/1923 | Hinchey . | |

(List continued on next page.)

FOREIGN PATENT DOCUMENTS

328171   11/1919   (DE) .

*Primary Examiner*—John J. Wilson
*Assistant Examiner*—Melba Bumgarner
(74) *Attorney, Agent, or Firm*—Senniger, Powers, Leavitt & Roedel (57) ABSTRACT

A dental prophy angle having a forwardly opening end formation and a closure which overlaps the end formation. The angle has a drive shaft having no lengthwise parting line, such that smoothness of operation is improved.

31 Claims, 5 Drawing Sheets

| Patent No. | Date | Name | Class |
|---|---|---|---|
| 1,465,690 | 8/1923 | Smith . | |
| 1,483,158 | 2/1924 | Chott . | |
| 1,497,759 | 6/1924 | Lowe . | |
| 1,499,345 | 7/1924 | Chott . | |
| 1,499,346 | 7/1924 | Chott . | |
| 1,522,757 | 1/1925 | Thiedemann . | |
| 1,534,816 | 4/1925 | Thiedemann . | |
| 1,534,817 | 4/1925 | Thiedemann et al. . | |
| 1,535,187 | 4/1925 | Terry . | |
| 1,548,180 | 8/1925 | Brown et al. . | |
| 1,559,011 | 10/1925 | Skinner . | |
| 1,593,733 | 7/1926 | Terry . | |
| 1,620,990 | 3/1927 | Brothers . | |
| 1,631,444 | 6/1927 | Warren . | |
| 1,644,465 | 10/1927 | Chott . | |
| 1,694,636 | 12/1928 | Barker . | |
| 1,701,025 | 2/1929 | Young . | |
| 1,720,017 | 7/1929 | Touchstone . | |
| 1,759,075 | 5/1930 | Wahl . | |
| 1,837,938 | 12/1931 | Young . | |
| 1,838,982 | 12/1931 | Angell . | |
| 1,982,336 | 11/1934 | Wiseman . | |
| 2,010,421 | 8/1935 | Terry . | |
| 2,017,881 | 10/1935 | Wiseman . | |
| 2,039,278 | 5/1936 | Blanchard | 15/188 |
| 2,090,885 | 8/1937 | Clark . | |
| 2,093,006 | 9/1937 | Chott . | |
| 2,093,007 | 9/1937 | Chott | 15/246 |
| 2,135,933 | 11/1938 | Blair | 128/48 |
| 2,183,415 | 12/1939 | Thommies | 15/28 |
| 2,186,402 | 1/1940 | Bowen | 51/195 |
| 2,188,426 | 1/1940 | Blair . | |
| 2,194,187 | 3/1940 | Skinner | 279/9 |
| 2,202,299 | 5/1940 | Pelkey . | |
| 2,226,145 | 12/1940 | Smith | 15/29 |
| 2,263,808 | 11/1941 | Hutchinson . | |
| 2,300,828 | 11/1942 | Goldenberg . | |
| 2,393,751 | 1/1946 | Chott | 18/59 |
| 2,400,912 | 5/1946 | Britt et al. . | |
| 2,451,918 | 10/1948 | Chott . | |
| 2,469,261 | 5/1949 | Cooper . | |
| 2,738,528 | 3/1956 | Fridge, Sr. | 15/97 |
| 2,752,682 | 7/1956 | Wiseman . | |
| 2,766,470 | 10/1956 | Baker | 15/28 |
| 2,785,464 | 3/1957 | Hoffmeister . | |
| 2,789,352 | 4/1957 | Wiseman . | |
| 2,853,781 | 9/1958 | Hoffmeister . | |
| 2,911,660 | 11/1959 | Klemas et al. | 15/28 |
| 2,911,721 | 11/1959 | Staunt . | |
| 2,921,373 | 1/1960 | Wiseman . | |
| 2,943,343 | 7/1960 | Jankelson | 15/256.5 |
| 3,163,934 | 1/1965 | Wiseman . | |
| 3,389,468 | 6/1968 | Lewis et al. . | |
| 3,407,502 | 10/1968 | Richmond . | |
| 3,436,830 | 4/1969 | Richmond . | |
| 3,472,045 | 10/1969 | Nelsen et al. | 64/4 |
| 3,478,433 | 11/1969 | Richmond . | |
| 3,579,833 | 5/1971 | Colombo . | |
| 3,579,835 | 5/1971 | Levenson . | |
| 3,599,332 | 8/1971 | Graceffo . | |
| 3,599,333 | 8/1971 | Muhler . | |
| 3,621,577 | 11/1971 | Spinello . | |
| 3,624,908 | 12/1971 | Ricketts et al. . | |
| 3,629,944 | 12/1971 | Avakoff . | |
| 3,637,050 | 1/1972 | Hoffmeister | 184/6 R |
| 3,672,060 | 6/1972 | Elbofner et al. . | |
| 3,675,330 | 7/1972 | Drapen et al. . | |
| 3,691,636 | 9/1972 | Deuschle . | |
| 3,707,042 | 12/1972 | Talaga . | |
| 3,727,312 | 4/1973 | Durante . | |
| 3,727,313 | 4/1973 | Graham . | |
| 3,727,315 | 4/1973 | Spinello . | |
| 3,740,853 | 6/1973 | Brahler . | |
| 3,742,608 | 7/1973 | Jones . | |
| 3,757,419 | 9/1973 | Hopkins . | |
| 3,758,948 | 9/1973 | Bareth . | |
| 3,769,707 | 11/1973 | Condon . | |
| 3,775,849 | 12/1973 | Condon . | |
| 3,778,904 | 12/1973 | Melde . | |
| 3,789,462 | 2/1974 | Relch . | |
| 3,798,777 | 3/1974 | Reiter . | |
| 3,822,432 | 7/1974 | Skinner | 15/23 |
| 3,826,004 | 7/1974 | Graceffo . | |
| 3,858,323 | 1/1975 | Flatland . | |
| 3,858,368 | 1/1975 | Cocherell et al. | 51/358 |
| 3,871,097 | 3/1975 | Melde . | |
| 3,877,574 | 4/1975 | Killick | 206/368 |
| 3,913,594 | 10/1975 | Tsukamoto | 132/76.4 |
| 3,939,599 | 2/1976 | Henry et al. . | |
| 3,947,965 | 4/1976 | Flatland . | |
| 3,947,966 | 4/1976 | Lieb et al. . | |
| 3,964,166 | 6/1976 | Stahlman . | |
| 3,969,822 | 7/1976 | Fukuyama . | |
| 3,969,823 | 7/1976 | Nakanishi . | |
| 3,977,083 | 8/1976 | Leslie et al. . | |
| 3,977,084 | 8/1976 | Sloan . | |
| 4,014,099 | 3/1977 | Bailey . | |
| 4,020,522 | 5/1977 | Behrend | 15/180 |
| 4,021,918 | 5/1977 | Bailey . | |
| 4,053,983 | 10/1977 | Flatland . | |
| 4,055,897 | 11/1977 | Brix . | |
| 4,079,517 | 3/1978 | Zacharia . | |
| 4,117,597 | 10/1978 | Trist et al. . | |
| 4,123,845 | 11/1978 | Fatteleh . | |
| 4,182,041 | * 1/1980 | Girard | 433/115 |
| 4,183,140 | 1/1980 | Rieselman . | |
| 4,185,386 | 1/1980 | Nordin et al. | 433/82 |
| 4,185,388 | 1/1980 | Jarby | 433/125 |
| 4,234,308 | 11/1980 | Leonard | 433/127 |
| 4,253,832 | 3/1981 | Bailey | 433/115 |
| 4,259,071 | 3/1981 | Warden et al. | 433/166 |
| 4,266,933 | 5/1981 | Warden et al. | 433/82 |
| 4,268,252 | 5/1981 | Lustig et al. | 433/126 |
| 4,285,671 | 8/1981 | Lustig et al. | 433/126 |
| 4,292,027 | 9/1981 | Richmond | 433/127 |
| 4,295,829 | 10/1981 | Martinelli et al. | 433/99 |
| 4,295,830 | 10/1981 | Uchida | 433/115 |
| 4,310,310 | 1/1982 | Bailey | 433/126 |
| 4,321,039 | 3/1982 | Schuss et al. | 433/82 |
| 4,321,041 | 3/1982 | Lustig et al. | 433/133 |
| 4,348,180 | 9/1982 | Schuss | 433/126 |
| 4,365,956 | 12/1982 | Bailey | 433/115 |
| 4,381,792 | 5/1983 | Busch, Jr. et al. | 132/75.6 |
| 4,406,621 | 9/1983 | Bailey | 433/126 |
| 4,424,036 | 1/1984 | Lokken | 433/116 |
| 4,432,729 | 2/1984 | Fatteleh | 433/118 |
| 4,447,208 | 5/1984 | Lustig | 433/126 |
| 4,449,932 | 5/1984 | Lustig | 433/126 |
| 4,486,175 | 12/1984 | Fisher et al. | 433/104 |
| 4,486,176 | 12/1984 | Tardieu et al. | 433/133 |
| 4,490,113 | 12/1984 | Kawada | 433/104 |
| 4,490,114 | 12/1984 | Kleesattel et al. | 433/105 |
| 4,533,324 | 8/1985 | Nakanishi | 433/132 |
| 4,544,356 | 10/1985 | Gardella et al. | 433/122 |
| 4,564,354 | 1/1986 | Rosenstatter | 433/133 |
| 4,575,338 | 3/1986 | Maizenberg | 433/126 |
| 4,604,058 | 8/1986 | Fisher et al. | 433/127 |
| 4,753,594 | 6/1988 | Croll | 433/125 |
| 4,753,595 | 6/1988 | Schuss et al. | 433/133 |
| 4,795,343 | 1/1989 | Choisser | 433/116 |
| 4,842,516 | 6/1989 | Choisser | 433/132 |
| 4,854,870 | 8/1989 | Kofod | 433/166 |

| | | | | | | | | |
|---|---|---|---|---|---|---|---|---|
| 4,911,639 | 3/1990 | Jacklich | 433/102 | | 5,360,339 | 11/1994 | Rosenberg | 433/165 |
| 4,929,180 | 5/1990 | Moreschini | 433/166 | | 5,374,189 | 12/1994 | Mendoza | 433/125 |
| 5,007,831 | 4/1991 | Bierbaum et al. | 433/114 | | 5,380,202 | 1/1995 | Brahler | 433/166 |
| 5,007,832 | 4/1991 | Meller et al. | 433/126 | | 5,404,265 | 4/1995 | Mendoza | 433/166 |
| 5,020,994 | 6/1991 | Huang | 433/124 | | 5,423,679 | 6/1995 | Bailey | 433/125 |
| 5,022,857 | 6/1991 | Matsutani et al. | 433/85 | | 5,433,605 | 7/1995 | Strobl, Jr. | 433/112 |
| 5,028,181 | 7/1991 | Jenkins et al. | 409/215 | | 5,482,461 | 1/1996 | Yale | 433/125 |
| 5,028,233 * | 7/1991 | Witherby | 433/125 | | 5,484,284 | 1/1996 | Bailey | 433/125 |
| 5,040,978 | 8/1991 | Falcon et al. | 433/125 | | 5,498,159 | 3/1996 | Coss | 433/126 |
| 5,040,980 | 8/1991 | Heil | 433/127 | | 5,503,555 * | 4/1996 | Bailey | 433/126 |
| 5,083,922 | 1/1992 | Yale | 433/166 | | 5,507,644 | 4/1996 | Kivligham, Jr. | 433/166 |
| 5,120,220 | 6/1992 | Butler | 433/125 | | 5,531,599 | 7/1996 | Bailey | 433/125 |
| 5,131,846 | 7/1992 | Hall | 433/116 | | 5,542,846 | 8/1996 | Quinn et al. | 433/127 |
| 5,156,547 | 10/1992 | Bailey | 433/125 | | 5,571,012 | 11/1996 | Witherby et al. | 433/125 |
| 5,160,263 | 11/1992 | Meller et al. | 433/125 | | 5,584,690 | 12/1996 | Maassarani | 433/125 |
| 5,178,536 | 1/1993 | Werly et al. | 433/29 | | 5,642,995 | 7/1997 | Bailey | 433/115 |
| 5,178,538 | 1/1993 | Eckert | 433/166 | | 5,645,426 * | 7/1997 | Grim et al. | 433/125 |
| 5,209,658 | 5/1993 | Brahler | 433/125 | | 5,647,745 | 7/1997 | Badoz | 433/126 |
| 5,219,285 | 6/1993 | Meller et al. | 433/126 | | 5,653,591 | 8/1997 | Logé | 433/118 |
| 5,224,859 | 7/1993 | Kraenzle | 433/126 | | 5,667,383 | 9/1997 | Mendoza et al. | 433/132 |
| 5,267,860 | 12/1993 | Ingram, Jr. et al. | 433/116 | | 5,683,247 | 11/1997 | Bailey | 433/104 |
| 5,273,558 | 12/1993 | Nelson et al. | 51/298 | | 5,690,488 | 11/1997 | Spinello | 433/116 |
| 5,273,559 | 12/1993 | Hammer et al. | 51/298 | | 5,692,901 | 12/1997 | Roth et al. | 433/85 |
| 5,316,475 | 5/1994 | Rosenberg | 433/166 | | 5,704,786 | 1/1998 | Quinn | 433/128 |
| 5,328,369 | 7/1994 | Bailey | 433/125 | | 5,730,595 | 3/1998 | Bailey | 433/125 |
| 5,334,020 | 8/1994 | Eckert | 433/166 | | 5,749,728 | 5/1998 | Bailey | 433/125 |
| 5,340,310 | 8/1994 | Bifulk | 433/123 | | 5,772,435 | 6/1998 | Dorman | 433/126 |
| 5,340,311 | 8/1994 | Sakurai | 433/126 | | 5,775,905 | 7/1998 | Weissenfluh et al. | 433/166 |
| 5,340,312 | 8/1994 | Murase | 733/132 | | 5,797,743 | 8/1998 | Bailey | 433/126 |
| 5,348,473 | 9/1994 | Kivligham, Jr. | 433/114 | | 5,797,744 | 8/1998 | Rosenberg | 433/166 |
| 5,352,119 | 10/1994 | Sakural | 433/125 | | | | | |
| 5,354,200 | 10/1994 | Klein et al. | 433/72 | | | | | |

* cited by examiner

DENTAL PROPHYLAXIS ANGLE

BACKGROUND OF THE INVENTION

This invention relates to a dental appliance and, more specifically, to a dental prophylaxis angle (commonly called a "prophy angle").

Dental prophy angles typically include a hollow head on the end of a tubular body. One such angle is disclosed in Kraenzle U.S. Pat. No. Re 34,997. A drive shaft within the body drives a rotor in the head of the angle. At the rearward end of the angle, i.e., the end remote from the head, the drive shaft is driven by a drive mechanism. A prophylaxis cup ("prophy cup") is attached to the rotor. These angles are commonly constructed of lightweight, inexpensive plastic so that they are disposable and may be discarded after use, thus obviating the expense and inconvenience of sterilization. Inexpensive plastic materials do not lend themselves easily to use in connection with an angle which is sturdy and easily assembled and which operates smoothly and consistently. Designers of plastic prophy angles are continuously trying to improve such angles to make them more sturdy, operate more smoothly, operate with less friction, and to improve efficacy for cleaning and polishing teeth.

SUMMARY OF THE INVENTION

It is an object of this invention, therefore, to provide an improved dental appliance, more particularly, to provide an improved prophylaxis angle which is economical to manufacture, easily assembled, of sturdy construction, pleasing in appearance, and which operates smoothly and consistently.

Briefly, therefore, the invention is directed to a dental prophy angle having a forwardly opening forward end formation with a closure therefor which overlap each other when the closure is applied to the end formation, and cooperative locking elements for securing the closure in fixed position on the forward end formation.

In another aspect the invention is directed to a dental prophy angle having a closure and a forwardly opening end formation and a sealing rim for sealing the mating interface between the closure and the end formation.

The invention is also directed to a dental prophy angle having a cylindric bearing surface for a rotor, which surface has at least two bearing discontinuities therein formed by mating surfaces of a closure and a recessed end formation. The bearing discontinuities are engageable by a rotor ridge on the rotor upon rotation of the rotor, and the mating surfaces lie in planes which extend non-radially with respect to the rotor.

The invention is further directed to a dental prophy angle having a rotor bearing and a drive shaft bearing, one of which has a juncture discontinuity thereon formed by mating components of the angle. The juncture discontinuity has a segment which is not parallel to a longitudinal axis of the rotor bearing or drive shaft bearing on which lies the juncture discontinuity.

In another aspect the invention is directed to a dental prophy angle having a cylindric bearing surface for the rotor having a juncture discontinuity thereon formed by mating surfaces of a closure and a recessed end formation. The juncture discontinuity has a segment which is not parallel to the axis of the rotor.

The invention is further directed to a dental prophy angle having a drive shaft having a longitudinal axis, first and second opposite ends, and a first section on one side of a plane extending through the shaft generally transverse to the longitudinal axis. The first section extends from the plane to the first end of the shaft, and there is a second section on an opposite side of the plane extending from the plane to the second end of the shaft. The first section of the shaft has an outside diameter which does not substantially increase along the first section in a direction from the plane to the first end and the second section of the shaft has an outside diameter which does not substantially increase along the second section in a direction from the plane to the second end. As such, the shaft may be formed as an integral molded part in a mold having a parting line corresponding to the plane, the drive shaft being configured for insertion, rear end first, into the bore from the forward end of the tubular extension.

Still further, the invention is directed to a dental prophy angle having a drive shaft having an elongate shape and a longitudinal axis extending through a bore in the angle, which drive shaft is inserted into said bore, rear end first, from the forward end of the tubular extension, and which drive shaft is a molded piece having a mold parting line extending circumferentially of the shaft and not longitudinally of the shaft.

The invention is also directed to a dental prophy angle having a rotor rotary in a chamber on an axis transverse to the axis of a bore in the angle, the rotor having a driven gear with gear teeth adapted for engagement with the gear teeth of said drive gear. The rotor has a generally vertical cylindric section extending generally parallel to the rotor axis, the cylindric section being sized for engagement by the forward end of the drive shaft over a substantial area thereof to limit the forward movement of the drive shaft toward the rotor and thus limit the forward force applied to the driven gear by the driving gear.

In another aspect the invention is directed to a dental prophy angle having a rotor rotary in a chamber on an axis transverse to the axis of a bore in the angle, with the rotor having a driven gear with gear teeth adapted for engagement with gear teeth of a drive gear, and the rotor having a generally vertical cylindric section extending below the driven gear and generally parallel to the rotor axis. The cylindric section is sized for engagement by the forward end of the drive shaft over a substantial area thereof to limit the forward movement of the drive shaft toward the rotor and thus limit the forward force applied to the driven gear by the driving gear.

The invention is further directed to a dental prophy angle having a drive shaft having a longitudinal axis, first and second opposite ends, and a first section on one side of a plane extending through the shaft generally transverse to the longitudinal axis. The first section extends from the plane to said first end of the shaft, and a second section on an opposite side of the plane extends from the plane to the second end of the shaft. The first section of the shaft has an outside diameter which does not substantially increase along the first section in a direction from the plane to the first end and the second section of the shaft has an outside diameter which does not substantially increase along the second section in a direction from the plane to the second end. As such, the shaft may be formed as an integral molded part in a mold having a parting line corresponding to said plane. The drive shaft also has two spaced-apart shaft bearing surfaces which contact two spaced-apart bore bearing surfaces inside the tubular extension.

In another aspect the invention is directed to a dental prophy angle having an elongate one-piece hollow body of molded plastic material comprising a tubular handle and a tubular extension extending from the handle at one end thereof. There is a gate imperfection on an external surface of the elongate hollow body which is covered over and hidden from view upon securement of the rotor and drive shaft in place, the gate imperfection being remote from bearing surfaces for the rotor and the drive shaft.

Other objects and features of the invention will be in part apparent and in part pointed out hereinafter.

DETAILED DESCRIPTION OF THE PREFERRED EMBODIMENTS

Figure 1:
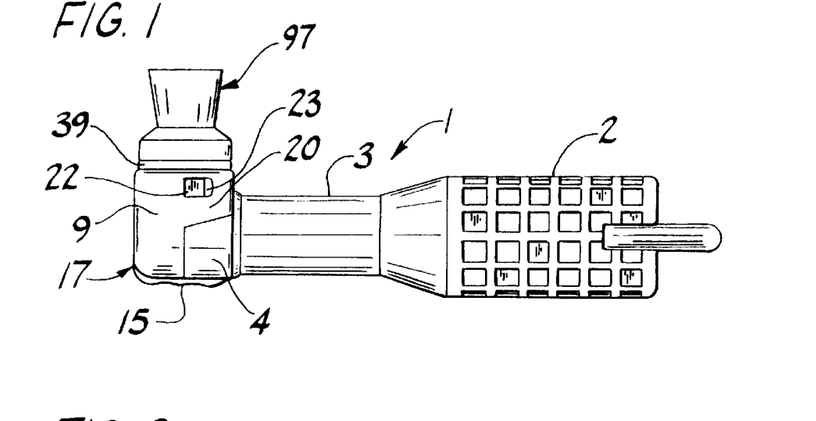
FIG. 1 is a side elevation of an assembled prophy angle of the invention.
Figure 2:
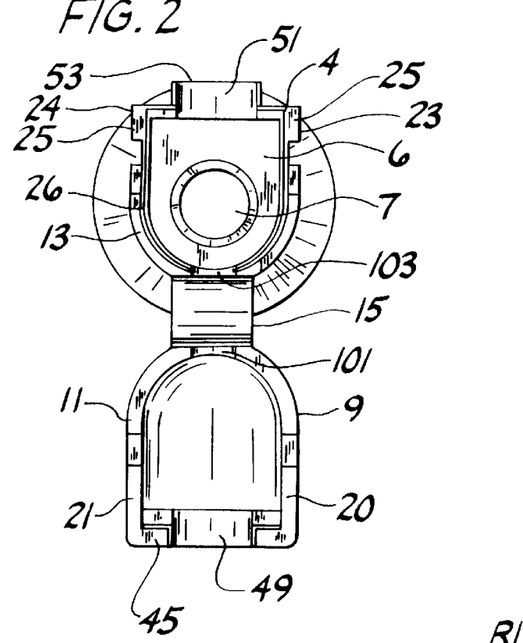
FIG. 2 is an end view from the forward end of the body of the angle, open for assembly.

Referring to FIG. 1, there is generally indicated at 1 an elongate hollow body of the prophy angle of the invention. The prophy angle includes a tubular handle 2 and a tubular extension 3 extending forwardly from the handle 2. An end formation 4 is positioned at the forward end of the tubular extension 3. As shown in FIG. 2, the formation 4 opens forwardly and defines a forwardly opening recess indicated generally at 6. Because this recessed end formation opens in a forward direction, access is provided to the interior of the tubular extension 3 and handle 2 which define a bore 7.

Figure 4:
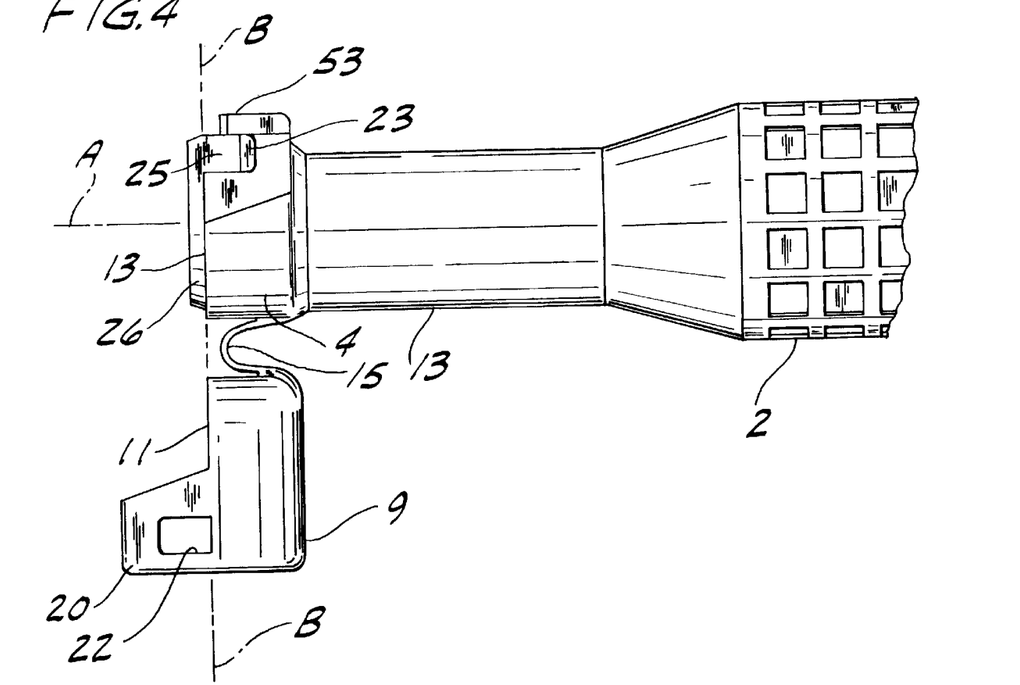
FIG. 4 is partial side elevation of the body, open for assembly.
Figure 7:
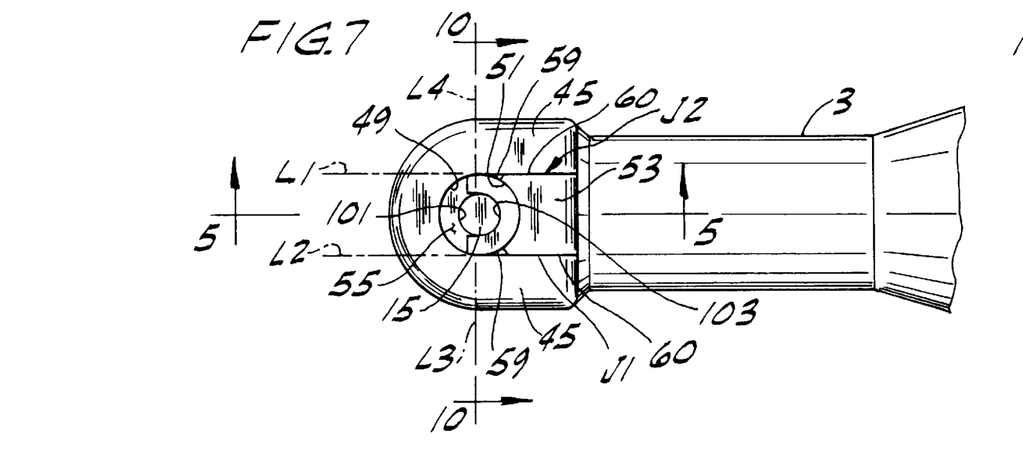
FIG. 7 is a partial top view of the body with the closure applied to the end formation, the rotor being removed to illustrate the rotor bearing.

A closure 9 is shown in its secured, closed position applied to end formation 4 in FIGS. 1 and 7 and in its open, unapplied, unsecured position away from formation 4 in FIGS. 2 and 4. Closure 9 has a rim 11 which mates with a rim 13 on the end formation 4 when the closure is applied to the end formation. When closure 9 is in its unapplied position, access to bore 7 of the tubular extension is provided. Closure 9 is movable between secured and unsecured positions and, at the manufacturer's option, may be a separate piece from, or integral with, formation 4. In the preferred embodiment, the closure 9 is attached to formation 4 by means of an integral hinge 15. Hinge 15 in the current invention is slightly wider than the hinge 12 in Re. 34,997 to facilitate molding. The entire disclosure of Re. 34,997 is specifically incorporated herein by reference. The wider hinge 15 of the current design also provides added strength to the assembled angle. The handle 2, tubular extension 3, end formation 4, hinge 15 and closure 9 are integral, preferably co-molded as a single plastic piece of a material such as nylon 6/6, e.g., as available under the trade name Zytel 101 available from DuPont de Nemours Co. Molding the closure, hinge and body as a single piece facilitates assembly of a sturdy, smoothly operating angle. The wall thickness of the body is preferably relatively uniform to minimize inconsistent shrinkage problems during molding.

The tubular handle 2 and extension 3 of the body 1 defining bore 7 have a longitudinal axis indicated at A in FIG. 4. The rim 11 of closure 9 mates with the rim 13 of formation 4 generally in a plane B transverse to axis A. When closure 9 is in its closed, secured position, applied to formation 4, the closure 9 and the forwardly opening recess 6 (FIG. 2) defined by the recessed end formation 4 cooperate to form a hollow head, generally designated 17, defining a chamber 19 (FIG. 5) at the forward end of tubular extension 3.

Figure 6:
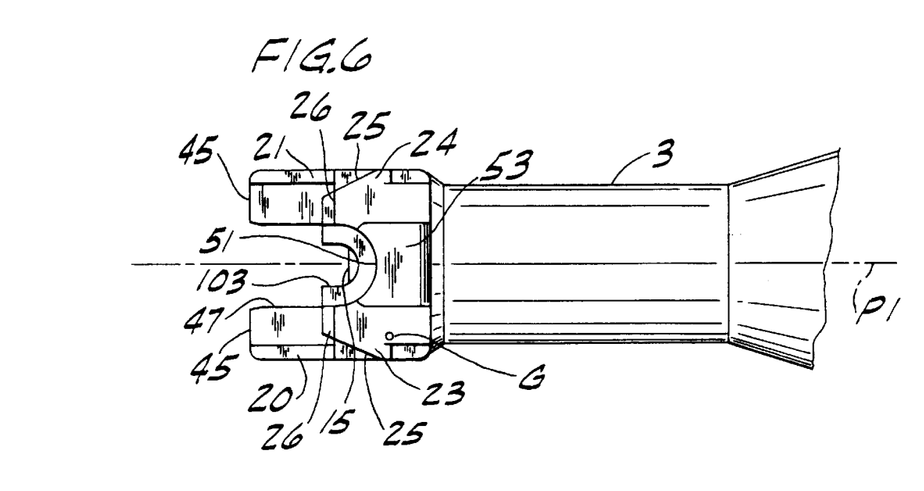
FIG. 6 is a partial top view of the body with the closure away from the end formation.

The closure 9 and end formation 4 are formed with securement extensions and cooperable locking elements to facilitate securement of the closure to the end formation. In the preferred embodiment these securement extensions comprise a first securement extension 20 on closure 9 at one side of the head 17 and a second securement extension 21 on the closure 9 at an opposite side of the head. Each securement extension may be in the form of a projecting flap having an opening 22 therein (see FIG. 4). In this preferred embodiment the locking elements comprise first and second lugs 23, 24 on the end formation at opposite sides of the head, as shown in FIGS. 4 and 6. The lugs protrude laterally from the end formation and are adapted for a snap fit reception in respective openings 22 in the securement extensions (FIG. 4). As can be seen in FIG. 6, the lugs 23 and 24 have upper inclined surfaces or ramps 25 which are engageable by respective securement extensions 20, 21 on the closure 9 when the closure is moved toward its secured position. The ramps function to force the securement extension outwardly as the closure is applied until the openings 22 move into registration with the lugs, at which time the extensions spring back for reception of the lugs in respective openings to snap lock the closure in its operative position, fully applied to the end formation. This engagement is shown in FIG. 1. When the closure 9 is locked to the end formation 4, the securement extensions or flaps 20, 21 extend rearwardly toward the handle 2 and overlap the end formation 4. Preferably, the securement extensions extend all the way to the rearward edge of the end formation.

The securement extensions 20, 21 of the present invention provide a more secure attachment of the closure 9 to the end formation 4 than the latch elements 18 and recesses 19 described in FIG. 2 of Re. 34,997. Latch elements 18 of Re. 34,997 extend forward from rim 4A of end formation 4 such that their size is limited by the size of bearing recesses 38 and 39. In particular, the latch elements and recesses shown in FIG. 2 of Re. 34,997 must be small enough that they do not interfere with or weaken the bearing recesses. Thus the bearing recesses limit the available latch sizes and configurations in this prior design. This problem is solved by the present invention because the cooperative locking elements, i.e., lugs 23 and 24 and openings 22, are on opposite sides of the end formation 4 rather than on the rim where the bearing recesses mate.

Other locking configurations consistent with the above are contemplated as being within the scope of this invention. For example, in one alternative embodiment, the locations of the securement extensions 20, 21 and lugs 23, 24 are reversed. In this embodiment the securement extensions 20, 21 are on the end formation 4 and extend forwardly therefrom, and the lugs 23, 24 extend laterally from opposite sides of the closure 9 for snap reception in openings in the securement extensions on the end formation. It is also contemplated that the lugs could take other configurations and vary in number and location without departing from the scope of this invention.

As shown in FIG. 4, the end formation 4 has a sealing rim 26 thereon which is overlapped by the closure 9 when the closure is applied to the end formation. The sealing rim 26 projects forwardly from the end formation and wraps around the top thereof as shown in FIG. 6. In an alternative embodiment (not shown), the sealing rim is on the closure and extends rearwardly from the closure. Inasmuch as it is preferred to used lubricant such as petroleum jelly to facilitate operation of the angle, the sealing rim functions to provide a seal for the mating interface between the closure 9 and the end formation 4 to minimize leakage of such fluid lubrication out of the chamber 19. The rim also functions to minimize leakage of abrasive material into the chamber. The sealing rim 26 also functions as a registration means to align and hold the closure 9 in proper position with respect to the end formation 4, as well as to further stabilize the interface between the closure and end formation upon securement of the closure to the end formation.

Figure 3:
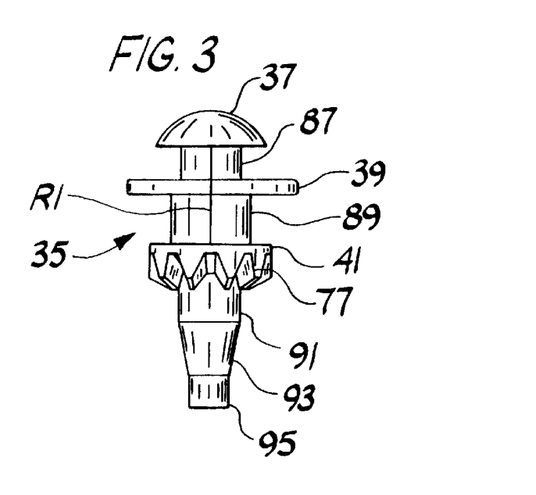
FIG. 3 is a side elevation of the rotor of the angle.
Figure 9:
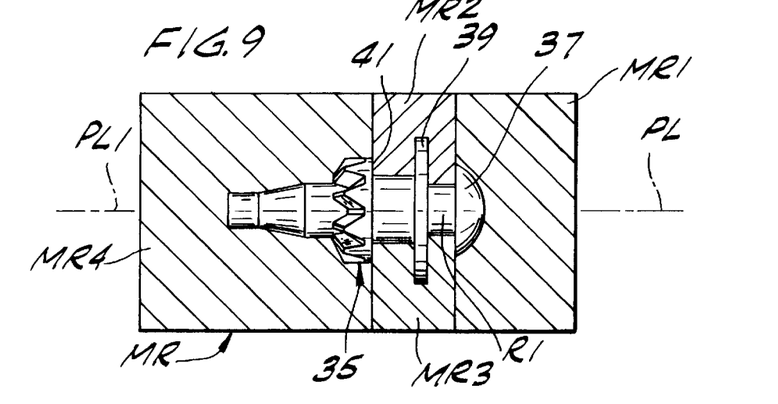
FIG. 9 is an elevation of the rotor of the prophy angle of the invention in a mold cavity of a mold in which the rotor is molded, the mold being shown schematically and sectioned.

Referring to FIGS. 3 and 9, a rotor for the angle of the present invention is designated generally by the reference numeral 35. The rotor has spaced-apart enlarged diameters defined by a button 37, a radial flange defining a shelf 39, and a driven gear shoulder 41. As a practical matter, this construction requires the rotor 35 to be molded with a parting line extending generally parallel to the longitudinal axis of the rotor. (The upper section of the rotor cannot be molded with the parting line in a plane transverse to the longitudinal axis of rotor because the spaced-apart enlarged diameters would prevent separation of the mold pieces.) As shown in FIG. 9, mold MR comprises mold sections MR1, MR2, MR3, and MR4, and parting line PL1 extending generally parallel to the longitudinal axis of the rotor. During the molding process, as plastic material is introduced into the mold cavity under pressure, small amounts of material will be forced from the mold cavity into the interface area between mold sections at the area corresponding to the parting line of the mold aligned with PL1. When this material solidifies it forms a small parting line ridge R1 on the rotor 35. This ridge R1 extends along opposite sides of the rotor from the bottom of the button to the top of the driven gear, the result being that the exterior surface of the rotor is not perfectly smooth. The ridge R1 extends generally longitudinally with respect to the rotor axis, although it strays from longitudinal where it must conform to the contours on the rotor, such as the shelf 39.

Figure 10:
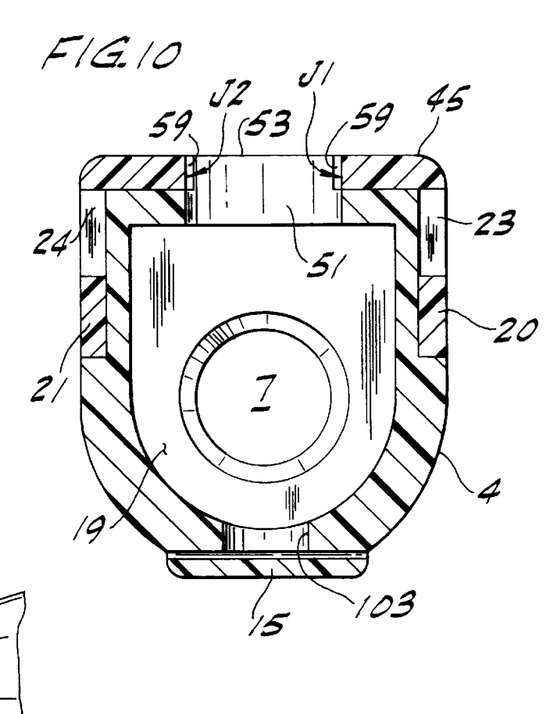
FIG. 10 is an enlarged section on line 10—10 of FIG. 7.

The securement extensions 20, 21 on the closure 9 wrap around the upper end of the closure 9 to form an upper end panel 45. As illustrated in FIGS. 6 and 7, the upper end panel 45 has a slot 47 therein extending forward from a rearward edge of the panel. The slot 47 is defined by a pair of substantially parallel side edges connected by a generally semi-circular end edge which defines a generally semi-circular bearing recess 49. When the closure 9 is applied to the forward end formation 4, this bearing recess combines with a generally semi-circular bearing recess defined by a semi-circular surface 51 of a bearing structure 53 on the forward end formation 4 to form a circular bearing 55 for the rotor. As shown in FIG. 7, the side edge surfaces of the slot 47 in the upper end panel 45 of the closure 9 interfit with (and preferably contact) opposite side surfaces of this bearing structure 53. The bottom (inside) surfaces of the upper end panel 45 on opposite sides of the slot 47 also interfit with (and preferably contact) the top surfaces of the end formation 4 on opposite sides of the bearing structure 53. These interfitting surfaces, which may be referred to as mating surfaces, form junctures J1, J2 between the closure and the end formation. As shown in FIGS. 5A, 7 and 10, these junctures form bearing discontinuities 59A, B, C in the rotor bearing surface and head discontinuities 59 (e.g., small gaps in FIG. 7) at the end of discontinuity lines 60 on the upper face of the head 17. As shown in FIGS. 5A, 7 and 10, these junctures form bearing discontinuities 59A, B, C in the rotor bearing surface and head discontinuities 59 (e.g., small gaps in FIG. 7) on the upper face of the head 17. The head discontinuities at junctures J1 and J2 and portions of the bearing discontinuities lie substantially in two spaced-apart generally parallel planes (L1 and L2 in FIG. 7) which extend generally longitudinally with respect to the tubular extension 3.

As noted above, the rotor 35 of the present invention is preferably a molded plastic part having a longitudinally extending ridge R1 corresponding to the parting line PL1 of the mold MR in which it is formed. During rotation of the rotor in the bearing, this ridge R1 engages the aforementioned discontinuities. The portion of the ridge which is under shelf 39 engages the head discontinuities (formed by the junctures J1 and J2) as it wipes over the top exterior face of upper end panel 45. However, it is believed that a configuration in which the junctures J1, J2 of the mating surfaces at 59 lie in non-radial planes with respect to the rotor 35 results in reduced shock or impact each time the rotor ridge R1 wipes over the discontinuities, which in turn results in smoother operation of the angle. In contrast, from FIGS. 1 and 3 of Re. 34,997 it is evident that the comparable junctures in the prior design are colinear with lines L3 and L4 in the present FIG. 7, and that such junctures lie in planes which extend radially with respect to the rotor, producing an operation which is not as smooth as the present invention.

Turning to FIG. 5A, it will be observed that the bearing surface discontinuity formed by the juncture J1 comprises a plurality of segments designated 59A, 59B and 59C. Segment 59A extends down from the top of the bearing a distance somewhat less than the full height of the bearing (slightly less than one-half the overall axial length of the bearing as shown in FIG. 5A). Segment 59A is generally aligned with, and preferably generally parallel to the longitudinal axis of the bearing 55 and the coincident longitudinal axis of the rotor 35 when the rotor is positioned in the bearing. Segment 59B extends from the lower end of segment 59A in a direction not parallel to, and preferably transverse to, and more preferably perpendicular to, the longitudinal axes of the bearing and rotor. Segment 59C is aligned with, and preferably generally parallel to, the longitudinal axes of the bearing and rotor and extends down from the end of segment 59B to the bottom of the bearing 55. Thus, the discontinuity segments 59A, 59B and 59C do not lie on a continuous straight line parallel to the longitudinal axis of the rotor and to the rotor ridge for the entire height of the bearing from the top of the bearing to the bottom of the bearing. (The configuration of the discontinuity 59 formed by the juncture J2 on the opposite side of the bearing mirrors that described above for J1, and is therefore not shown.) Consequently, as rotor ridge R1 wipes over the discontinuity segment 59A which is parallel to the rotor ridge, the rotor ridge is fully supported by the continuous surface of the bearing below 59A, so that impact or shock between the rotor ridge and the discontinuity at 59A is reduced or eliminated. Similarly, as rotor ridge R1 wipes over segment 59C which is parallel to rotor ridge, the rotor ridge is fully supported by the continuous surface of the bearing above 59C, so that impact or shock between the rotor ridge and the discontinuity at 59C is reduced or eliminated. In contrast, the comparable juncture in the design of Re. 34,997 lies in a continuous straight line parallel to the longitudinal axis of the rotor ridge along the entire height of the bearing surface, so that impact or shock between the rotor ridge and the juncture is more severe than in the current design.

The principle illustrated in FIG. 5A is applicable to other cylindric bearing surfaces formed by mating components such that they have juncture discontinuities thereon. For example, one embodiment of the current invention is a modification of the prophy angle of U.S. Pat. No. 5,028,233, FIGS. 3–6 and the text from column 1, line 59 to column 2, line 12 of which are expressly incorporated herein by reference. The circumferential bearing rings 16 and 18 in the '233 design are modified according to the current invention such that each juncture discontinuity formed in the cylindric bearing surfaces of bearing rings 16 and 18 by the juncture between components 10 and 11 has a segment which is not parallel to the longitudinal axis of drive shaft 9 in the '233 design. In particular, each bearing ring is designed like bearing surface 55 in current FIG. 5A. As such, as any lengthwise ridge in drive shaft 9 wipes over the cylindric bearing surface of 16 and 18, impact or shock between the ridge and the discontinuity is reduced or eliminated as described above. Drive shaft 9 does, in fact, have such a lengthwise ridge in view of its spaced apart enlarged diameters at 17, 13 and 14, which prevent it from being molded without a lengthwise parting line. In accordance with this invention, therefore, there is a generally cylindric rotor bearing and a generally cylindric drive shaft bearing, and at least one of the rotor bearing and drive shaft bearing have a juncture discontinuity thereon formed by mating components of the angle. This juncture discontinuity has a segment which is not parallel to the longitudinal axis of the rotor bearing or drive shaft bearing on which it is formed.

Figure 5:
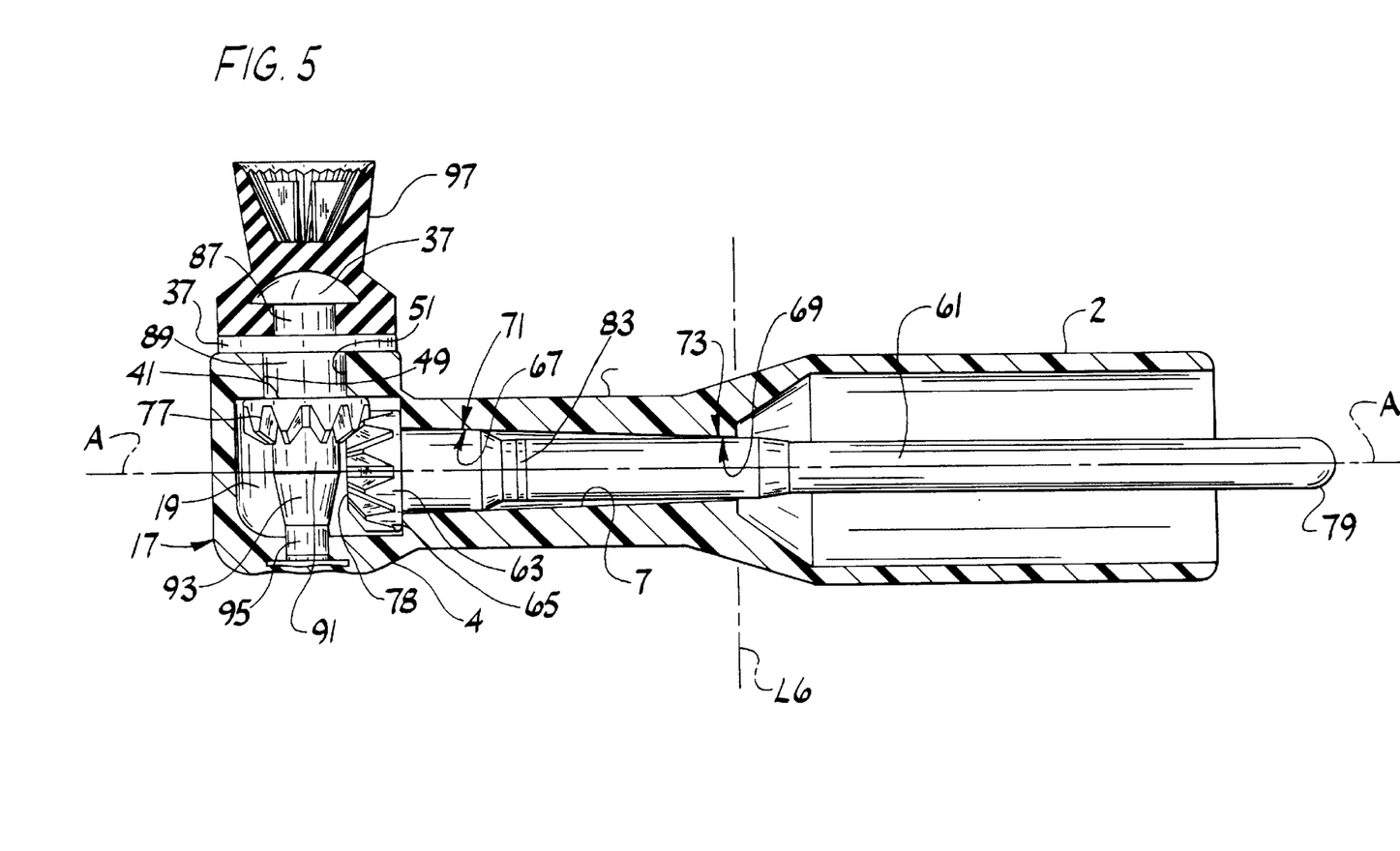
FIG. 5 is a sectional side elevation of the assembled angle along line 5—5 of FIG. 7 showing the rotor mounted in the angle.
Figure 5A:
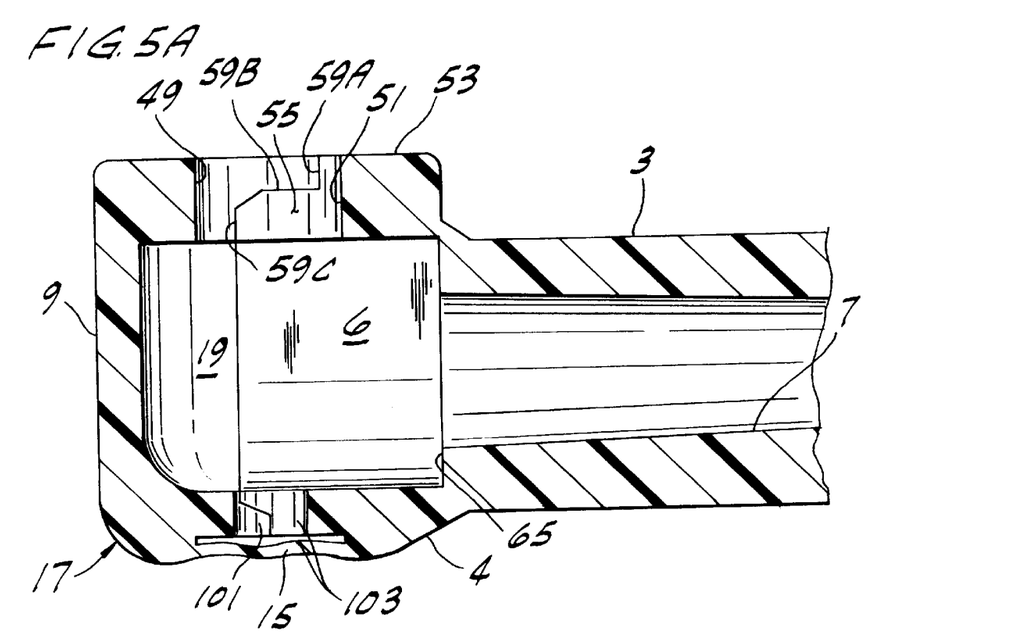
FIG. 5A is a view similar to FIG. 5 but with the rotor and drive shaft removed.

Turning to FIG. 5, a drive shaft 61 is positioned inside the bore 7 through the body 1, generally coaxial with bore axis A. The drive shaft has a gear 63 at its forward end. When the prophy angle is in assembled condition, the forward end of drive shaft 61 and drive gear 63 extend into the chamber 19 formed by the hollow head 17 of the angle. In this particularly preferred embodiment, gear 63 is of larger diameter than the bore 7 and engages the forward end of tubular extension 3 at 65 to hold the drive shaft against rearward movement in the bore. The drive shaft 61 also includes spaced-apart shaft bearing surfaces 67 and 69 which make bearing contact with the interior of the tubular extension at locations 71 and 73, respectively, which are spaced-apart bore bearing surfaces, for facilitating smooth rotation of the drive shaft within the bore. Chamber 19 houses rotor 35 such that teeth of gear 63 on the drive shaft 61 mate with the teeth of gear 77 on the rotor. The respective gears are shown here as Gleason type gears but may be other bevel or other type gears. Drive shaft 61 is driven at its rearward end in conventional fashion and thereby drives rotor 35 which is rotary in the chamber 19. Drive shaft 61, as well as rotor 35, are preferably molded from a plastic material such as acetal, e.g., as available under the trade name Delrin 500 available from DuPont de Nemours Co.

Figure 8:
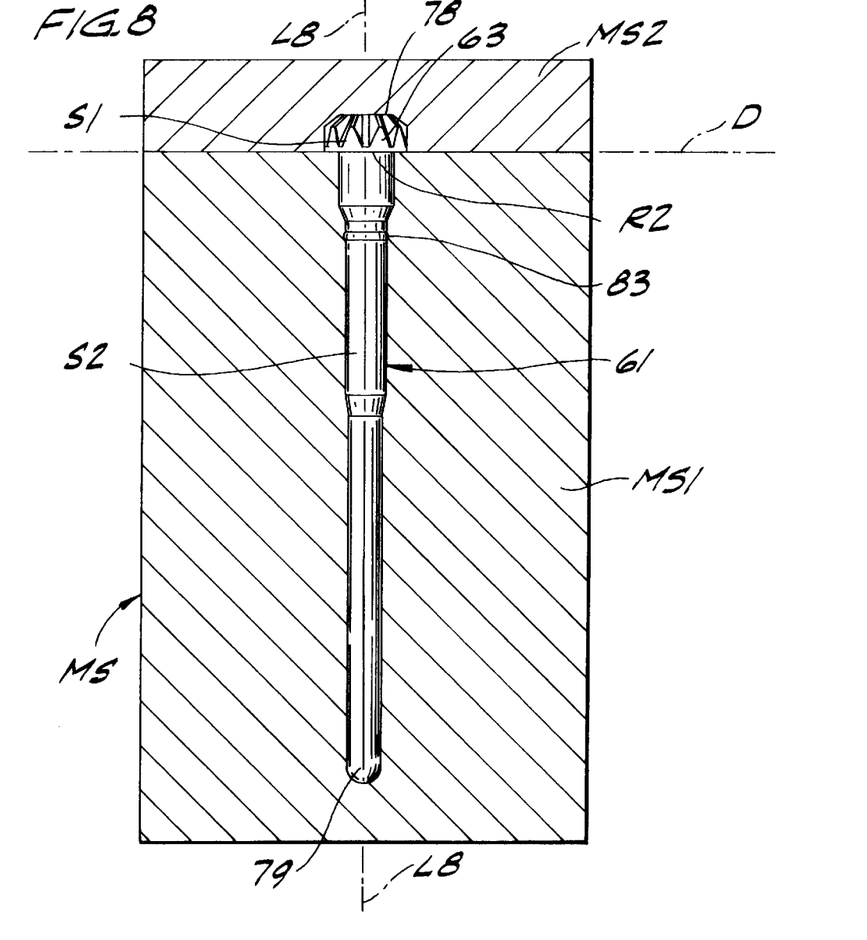
FIG. 8 is an elevation of the drive shaft of the prophy angle of the invention in a mold cavity of a mold in which the drive shaft is molded, the mold being shown schematically and sectioned.

Drive shaft 61 is preferably molded as shown in FIG. 8 with the drive shaft extending lengthwise from a lower mold half MS1 upwards to an upper mold half MS2 of a two-piece mold MS. This molding configuration is especially advantageous because it produces a parting line ridge R2 on the shaft only at the interface D in FIG. 8. This ridge R2 extends circumferentially with respect to the drive shaft 61. Importantly, the drive shaft is not formed with a lengthwise parting line ridge. A lengthwise parting line ridge of the type typical in the prior art has the disadvantage of causing the angle to run rougher as the ridge wipes over surfaces on the interior of the angle during rotation of the drive shaft. In the drive shaft 61 of the invention, the parting line ridge R2 is circumferential and therefore does not result in irregular, repetitive impact with any surfaces in the angle.

Referring again to FIG. 8, the drive shaft 61 has a longitudinal axis L8, a first end 78 corresponding to a front surface of gear 63, and a second end 79 at the opposite end of the shaft. A plane D extends through the shaft generally transverse to longitudinal axis L8. This plane divides the shaft into a first shaft section S1 on one side of the plane and a second shaft section S2 on the opposite side of the plane. The first section S1 extends from the plane D to the first end 78 of the shaft, and the second section S2 extends from the plane to the opposite, or second end 79 of the shaft. As can be seen in FIG. 8, the first section S1 of the shaft has an outside diameter which does not substantially increase along the first section in a direction (upward) from the plane D to the first end 78. Similarly, the second section S2 of the shaft has an outside diameter which does not increase substantially along the second section in a direction (downward) from the plane D to the second end 79. This configuration allows the shaft to be formed as an integral molded part in a two-piece mold MS having a parting line corresponding to plane D. In particular, since there is no increased diameter in the first section S1 of the shaft in the direction up from the plane D to the end at 78, the upper half MS2 of the mold can be removed so that the shaft remains in the lower half MS1 of the mold; and since there is no substantially increased diameter in the lower half MS1 of the mold in the direction from the plane D down to the second end 79 of the shaft, the completed shaft 61 can then readily be removed from the lower half MS1 of the mold. The only slightly increased diameter in the second (lower) section S2 of the shaft is due to surface contour 83 which is adapted to frictionally (but releasably) engage the mold MS to retain the second (lower) section of the shaft in place in the mold when the upper mold half is removed from the lower mold half, as will be explained in greater detail later. However, the increased resistance provided by this surface contour 83 is not so great as to prevent removal of the shaft from the mold, and it therefore does not interfere with allowing the shaft to be formed as an integral molded part in a two-piece mold having a parting line corresponding to plane D.

The drive shaft 61 of the invention has a further advantage due to the absence of a lengthwise parting line ridge. The portion of the drive shaft 61 extending rearwardly from the body 1 of the angle as shown in FIGS. 1 and 5 is gripped by a gripping mechanism such as a collet on a drive mechanism such as is typically used by dentists. Because the drive shaft is perfectly round and has no lengthwise parting line ridge, it is gripped evenly around its entire circumference by the gripping mechanism. In contrast, the lengthwise parting line ridges on other drive shafts interfere with the ability of the gripping mechanism to grip the entire circumference tightly. Another problem with a drive shaft having a lengthwise parting line ridge is that when the drive shaft is inserted into the drive mechanism, some of the ridge material can be shaved off by the gripping mechanism, leaving shavings in the drive mechanism. Over time and after repeated insertions of new drive shafts into a drive mechanism, these shavings accumulate unless cleaned out and can interfere with smooth operation of the drive mechanism. Problems arising from these shavings are eliminated by use of the drive shaft of the present invention.

A drive shaft such as that shown in Re. 34,997 must be molded with a lengthwise parting line because it has increased diameters such as spaced-apart bearings 40 and 41. These increased diameters 40 and 41 of Re. 34,997 prevent molding in a manner where the drive shaft extends lengthwise from one mold half into another mold half, for example vertically as shown in FIG. 8, because the increased diameters would prevent separation of the mold halves. In particular, if the drive shaft 20 of Re. 34,997 were molded with a circumferential parting line at, for example, location 41, the increased diameters at 22 and 40 would prevent separation of the mold halves.

Referring again to FIG. 8, the purpose of the surface contour 83 on the shaft is to provide a means for frictionally (but releasably) retaining the drive shaft 61 in mold half MS1 when mold half MS2 is removed. This surface contour may be in the form of a recess or a ridge and is imparted to the shaft by a mating contour on the interior of the mold cavity of mold MS. In this particular embodiment, the surface contour 83 is a raised collar (sometimes referred to as a "puller ring") extending circumferentially around the shaft. The collar 83 is integral with the shaft, being formed by the introduction of plastic material into a circular recess in the mold cavity. The collar 83 provides a degree of frictional engagement or tension with the mating recess in the mold, thus retaining the drive shaft 61 in the mold when mold half MS2 is separated from mold half MS1 upon completion of molding. This retention is releasable in that the collar 83 is sufficiently small in outside diameter that the tension created thereby is overcome by force applied by either grasping the first (upper) section S1 of the shaft and pulling the shaft out of the mold, or by ejecting the shaft out of the mold with an ejector pin (not shown) or the like in the bottom half MS2 of the mold. The collar 83 thus constitutes a slightly increased diameter with respect to the shaft, but the diameter is not so large as to prevent molding with only a circumferential parting line (i.e., with no lengthwise parting line). Stated another way, surface contour 83 does not prevent the shaft from being formed as an integral molded part in a two-piece mold having a parting line corresponding to D. The collar preferably increases the diameter of the drive shaft by less than about 0.005 in. when compared to the diameter of the drive shaft immediately above the collar.

As shown in FIG. 5, the bore 7 through the extension 3 is tapered from the forward end of the extension to the rearward end of the extension. The drive shaft 61 has spaced-apart first and second shaft bearing surfaces 67 and 69 which engage corresponding spaced-apart bearing surfaces on the tapered bore wall at 71 and 73, respectively. Significantly, the tapered configuration of the bore 7 provides two bearing contact areas which are spaced apart to provide operational stability yet relatively small in terms of overall bearing area to avoid overheating, and both objectives are achieved by using a shaft without increased-diameter bearing surfaces. It is preferred that the bearing contact areas be between about 0.050 inch and about 0.150 inch wide and be spaced apart as far as possible. In one preferred embodiment the bearing contact areas at 71 and 73 are about 0.070 inches wide, and the bearing surfaces are about ½ inch apart.

In FIG. 3 the rotor 35 is shown in its preferred embodiment as having (from top to bottom) button 37, a button support 87, shelf 39, an upper shank section 89, gear shoulder 41, driven gear 77, an intermediate cylindric shank section 91 below the driven gear, a reduced diameter clearance shank section 93, and a shank end section 95. The button 37 is provided for attachment of a prophy cup, but alternatively the rotor 35 may be configured to mount a burr or other dental tool to be rotatably driven, such as a brush. The button 37 is shaped to receive and retain a prophylaxis cup, generally designated 97, by snap engagement. Shelf 39 bears on closure 9 and end formation 4 and supports cup 97 as shown in FIGS. 1 and 5. Shelf 39 prevents downward movement of the rotor 35 relative to the chamber 19, and shoulder 41 prevents upward movement of the rotor relative to the chamber, as can be seen in FIG. 5.

The intermediate cylindric shank section 91 of the rotor 35 is so positioned and configured that it is disposed immediately adjacent the upper half of gear 63 on the drive shaft 61 when the angle is assembled, as shown in FIG. 5. As a result, shank section 91 is engageable by the forward face of the drive shaft at 78 to limit forward movement of the teeth of gear 63 into the driven rotor gear 77 when force is applied to the rear of the drive shaft. Upon application of such force, the front surface 78 of the drive shaft will contact the intermediate shank section 91 over a substantial area of the front surface 78 to limit the forward movement of the drive shaft toward the rotor. As a result, the teeth on the drive gear 63 are prevented from being driven too far or too forcefully into the driven gear 77. The cylindric surface of the intermediate shank section 91, which is generally coaxial with the rotary axis of the rotor 35, extends far enough below the driven gear 77 such that it is directly opposite substantially the entire upper half of the drive shaft gear 63 (i.e., the portion of the drive gear disposed above axis A in FIG. 5).

When the drive shaft gear 63 drives the rotor 35, the upper half of the drive gear and the rotor travel in generally the same direction, so there is little friction resulting from contact between the drive gear and the cylindric intermediate section 91 of the rotor. On the other hand, the bottom half of the drive gear 63 travels in a direction opposite to the direction of travel of the rotor 35. To reduce friction, the shank section 93 of the rotor is of reduced diameter to provide clearance between the rotor and the bottom half of the drive gear 63 (i.e., the portion of the drive gear disposed below axis A in FIG. 5). In the preferred embodiment, this clearance section 93 of the rotor is tapered, but it may take other reduced-diameter configurations so long as it does not contact the lower half of the drive gear 63, thereby avoiding friction therebetween.

The shank end extension 95 of the rotor 35 is received in a circular bearing cooperatively formed by recesses 101 and 103 (FIG. 2) in the closure 9 and forward end formation 4, respectively, when the closure is applied to the end formation. Smooth, sturdy rotational operation of the rotor is facilitated by the positioning of end extension 95 in this cooperatively formed circular bearing, as shown in FIG. 5.

In molding the tubular extension 3 and handle 2, the various irregular surfaces and increased diameters on the exterior of the end formation 4 and on the handle 2 require that the extension and handle be molded using a two-part mold having a parting line which extends lengthwise of the body 1. This results in the body having a lengthwise parting line ridge (not shown) on its exterior. The bore 7 through the handle and the tubular extension is formed by extending pins into the mold cavity from each end thereof. These pins meet at a location within the mold corresponding to line L6 in FIG. 5. The pins are removed after the molding process is completed. The pin inserted from the forward end is tapered to produce the interior taper between locations 71 and 73 in FIG. 5. A circumferential ridge line (not shown) forms along line L6 in FIG. 5 on the interior of the tubular extension 3 as fluid molding material forced into the interface between the pins solidifies, but because this ridge line is circumferential and continuous around the entire interior of the extension, rotation of the shaft 61 does not result in significant vibration. The drive shaft therefore advantageously contacts the extension 3 only at locations such as 71 and 73 which do not have an internal lengthwise parting line ridge or seam.

In molding plastic components such as prophy angles by injection molding it is necessary that there be a molding gate through which plastic flows into the mold cavity. One gating approach has been to use a gate which is positioned at the interface between two mold halves, i.e., at the mold parting line. A second gating approach is referred to as subgating, involving the use of a gate which enters the mold below the parting line. With either approach a runner is formed where plastic solidifies in the trough leading to the gate. If the gate and runner enter the mold cavity at the parting line, it is necessary to perform some manual or automatic manufacturing operation to shear the runner from the molded part. With subgating, the runner is automatically sheared from the molded part when the part is ejected from the mold. With this invention subgating is preferred in order to eliminate this extra manufacturing operation. To achieve proper shearing action, it is best that the gate enter the mold cavity at a point where there is a flat surface on the part so the runner is perpendicular to such surface. The present invention achieves this by having the subgate intersect the part at point G in FIG. 6 on the flat surface adjacent lug 23. The parting line ridges of the one-piece body 1 are generally along line P1 in this figure, and the runner is sheared from the molded part at point G when the part is ejected from the mold.

Once removed, the runners can be discarded or recycled. An optional approach is to employ heating elements in the mold proximate the runners to prevent the runner material from solidifying between molding operations. These hot runners, as they are called, however, are an extra expense in terms of materials, installation, maintenance, and associated inconvenience. This expense is balanced against the expense of wasted runner material if hot runners are not used. The current preference with this invention is to use a combination of hot runners and cold runners.

When subgating is not used, the gate inevitably results in an imperfection (indicated at G in FIG. 6) which is a blemish, burr or the like on the finished part, similar to a parting line ridge except at a point rather than along a line. To eliminate this imperfection it is necessary to sand, polish or clip material off, which is an extra manufacturing operation. Consequently, manufacturers are faced with the choice of leaving the imperfection on the part, where it detracts from its appearance and potentially its operation, or incur an extra manufacturing operation to remove the imperfection. Furthermore, where the decision is to leave the gate imperfection on the part, it is often necessary to recess it in a groove or the like so it will not serve as a snagging point. In the present invention, the imperfection left by gating (e.g., at G in FIG. 6) is located such that when the closure is applied to the end formation as shown in FIG. 7, the imperfection is covered by upper end panel 45. Because the imperfection is not in view on the assembled angle, there are no cosmetic or snagging problems associated with having the imperfection on an external surface of the angle after assembly. As such, the extra manufacturing operation of removing the imperfection is avoided. Also, because the imperfection is on an external surface of the tubular extension, its burr/blemish is remote from any bearing surface for a rotating rotor or drive shaft. Having this gate imperfection on a bearing surface would interfere with smooth operation of the angle. This interference is avoided by this invention because the gate imperfection is remote from the bearing surface. Furthermore, because the gate imperfection is covered over by a component (the closure) which assists in securing one of the drive shaft and rotor in place, there is no extra component required which functions only cover over the gate imperfection.

A prophy angle of the present invention is easy to assemble. The angle is initially provided in a condition where the closure 9 is away from the forward end formation 4 in a hingedly open position as shown in FIGS. 2, 4 and 6 providing access to the bore 7 and to the forwardly opening recess 6 defined by formation 4. With formation 4 opening forwardly, drive shaft 61 is readily inserted into bore 7 at the forward end of the body to a point where gear 63 engages the forward end of extension 3 at 65. Rotor 35 is placed in the forwardly opening recess in a position wherein the rotor gear 77 mates with the gear 63 of the drive shaft, wherein end extension 95 of the rotor is received in semicircular recess 103, and wherein the upper shank section 89 is received in the semicircular recess defined by surface 51 of the bearing structure 53 on end formation 4. With the rotor 35 thus positioned, closure 9 is applied to the recessed end formation 4 to define the chamber 19 which houses the rotor. Semicircular recess 101 mates with semicircular recess 103, and semicircular recess 49 mates with semicircular recess 51 in directly opposed relationship on opposite sides of a plane coincident with the rotor axis to form cylindric openings constituting bearings for the rotor 35. The rotor axis is generally coincident with the plane on which the rim 11 of closure 9 mates with rim 13 of the formation 4. The closure, rotor and drive shaft are secured in place by securement of the closure to the end formation 4 by the reception of lugs 23, 24 in the openings 22 in the securement extensions 20, 21 on the closure 9.

In view of the above, it will be seen that the several objects of the invention are achieved.

Although specific examples of the present invention and its application are set forth herein, it is not intended that they are exhaustive or limiting of the invention. These illustrations and explanations are intended to acquaint others skilled in the art with the invention, its principles, and its practical application, so that others skilled in the art may adapt and apply the invention in its numerous forms, as may be best suited to the requirements of a particular use.

What is claimed is:

1. A dental prophy angle comprising:
    an elongate hollow body comprising a tubular handle and a tubular extension extending from the handle at one end thereof, the tubular extension having a bore therethrough from the end thereof at the handle to its other end constituting its forward end, the tubular extension having at its forward end a recessed forward end formation defining a forwardly opening recess;
    a closure for said recess mating with said recessed forward end formation on said recess;
    said recessed forward end formation and said closure mating in directly opposed relationship on opposite sides of a plane generally transverse with respect the axis of said bore in the extension to define a hollow head with a chamber therein at said forward end of the tubular extension when the closure is applied to said recessed forward end formation;

a first securement extension on one of the closure and the forward end formation configured for overlapping an exterior surface of the other of the closure and forward end formation when the closure is applied to the end formation; and a first set of cooperative locking elements on the first securement extension and said other of the closure and forward end formation for securing the closure in fixed position on the forward end formation.

2. The dental prophy angle of claim 1 wherein said first set of cooperative locking elements comprises a first lug and a first opening for receiving said first lug.

3. The dental prophy angle of claim 2 wherein the first lug projects laterally from the forward end formation and has an inclined surface for biasing the first securement extension laterally outwardly as the closure is applied to the end formation, and wherein the first opening is in said first securement extension.

4. The dental prophy angle of claim 3 wherein the first securement extension is at one side of the head.

5. The dental prophy angle of claim 1 wherein the end formation has a sealing rim which extends forwardly from the end formation and which is overlapped by the closure when the closure is applied to the end formation to provide a sealing fit between the closure and the end formation.

6. A dental prophy angle comprising:

an elongate hollow body comprising a tubular handle and a tubular extension extending from the handle at one end thereof, the tubular extension having a bore therethrough from the end thereof at the handle to its other end constituting its forward end, the tubular extension having at its forward end a recessed forward end formation defining a forwardly opening recess;

a closure for said recess mating with said recessed forward end formation on said recess;

said recessed forward end formation and said closure combining to define a hollow head with a chamber therein at said forward end of the tubular extension when the closure is applied to said recessed forward end formation;

a first securement extension on one of the closure and the forward end formation configured for overlapping an exterior surface of the other of the closure and forward end formation when the closure is applied to the end formation;

a first set of cooperative locking elements on the first securement extension and said other of the closure and forward end formation for securing the closure in fixed position on the forward end formation; and a second securement extension on one of the closure and the forward end formation for overlapping the exterior surface of the other of said closure and said forward end formation, and a second set of cooperative locking elements on the second securement extension and on the other of said closure and said forward end formation for securing the closure in said fixed position, said first and second securement extensions being located on opposite sides of the head.

7. A dental prophy angle comprising:

an elongate hollow body comprising a tubular handle and a tubular extension extending from the handle at one end thereof, the tubular extension having a bore therethrough from the end thereof at the handle to its other end constituting its forward end, the tubular extension having at its forward end a recessed forward end formation defining a forwardly opening recess;

a closure for said recess mating with said recessed forward end formation on said recess at a mating interface between the closure and the end formation;

said recessed forward end formation of the tubular extension and said closure mating in directly opposed relationship on opposite sides of a plane generally transverse with respect the axis of said bore in the extension to define a chamber at said forward end of the tubular extension when said closure is applied to said recessed forward end formation;

a sealing rim for sealing the mating interface between the closure and the end formation;

a rotor rotary in the chamber on an axis transverse to the axis of the bore;

a drive shaft extending through said bore having a forward end in said chamber; and a gear on the forward end of the drive shaft mating with a gear on the rotor.

8. The dental prophy angle of claim 7 wherein said sealing rim extends forwardly from the end formation and is overlapped by the closure when the closure is applied to the end formation to provide a sealing fit between the closure and the end formation.

9. A dental prophy angle comprising:

an elongate hollow body comprising a tubular handle and a tubular extension extending from the handle at one end thereof, the tubular extension having a bore therethrough from the end thereof at the handle to its other end constituting its forward end, the tubular extension having at its forward end a recessed forward end formation defining a forwardly opening recess;

a closure for said recess mating with said recessed forward end formation on said recess at a mating interface between the closure and the end formation;

said recessed forward end formation of the tubular extension and said closure defining a chamber at said forward end of the tubular extension when said closure is applied to said recessed forward end formation;

a rotor rotary in the chamber on an axis transverse to the axis of the bore, the rotor having a raised ridge extending along an exterior surface of the rotor corresponding to the parting line of a mold;

the end formation and closure being formed with cooperative bearing recesses which mate to provide a generally cylindrical bearing for the rotor when the closure mates with the end formation;

a drive shaft extending through said bore having a forward end in said chamber; and a gear on the forward end of the drive shaft mating with a gear on the rotor;

said cylindric bearing comprising a cylindric surface having at least two bearing discontinuities therein formed by mating surfaces of the closure and the recessed end formation, said bearing discontinuities being engageable by said rotor ridge upon rotation of the rotor, said mating surfaces lying in planes which extend non-radially with respect to the rotor.

10. The dental prophy angle of claim 9 wherein each of said discontinuities comprises a segment which is not parallel to a longitudinal axis of said cylindric bearing.

11. The dental prophy angle of claim 9 wherein said chamber is within a head having an upper surface which contacts a shelf on said rotor upon rotation therefor, said upper surface having at least two head discontinuities therein formed by mating surfaces of the closure and the recessed end formation, said head discontinuities being engageable by said rotor ridge upon rotation of the rotor, said mating surfaces lying in planes which extend non-radially with respect to the rotor.

12. A dental prophy angle comprising:
- an elongate hollow body comprising a tubular handle and a tubular extension extending from the handle at one end thereof, the tubular extension having a bore therethrough from the end thereof at the handle to its other end constituting its forward end;
- a chamber at said forward end of the tubular extension;
- a rotor rotary in the chamber on an axis transverse to the axis of the bore;
- a drive shaft extending through said bore having a forward end in said chamber, said drive shaft having a lengthwise ridge; and
- a gear on the forward end of the drive shaft mating with a gear on the rotor;
- a generally cylindric rotor bearing for the rotor; and
- a generally cylindric drive shaft bearing for the drive shaft;
- said drive shaft bearing having a juncture discontinuity thereon formed by mating components of the angle, said juncture discontinuity having a segment which is not parallel to a longitudinal axis of said drive shaft bearing; and
- a continuous bearing surface adjacent said juncture discontinuity which supports the drive shaft as it wipes over said juncture discontinuity and thereby reduces impact between said lengthwise ridge in the drive shaft and said juncture discontinuity.

13. A dental prophy angle comprising:
- an elongate hollow body comprising a tubular handle and a tubular extension extending from the handle at one end thereof, the tubular extension having a bore therethrough from the end thereof at the handle to its other end constituting its forward end, the tubular extension having at its forward end a recessed forward end formation defining a forwardly opening recess;
- a closure for said recess mating with said recessed forward end formation on said recess at a mating interface between the closure and the end formation;
- said recessed forward end formation of the tubular extension and said closure defining a chamber at said forward end of the tubular extension when said closure is applied to said recessed forward end formation;
- a rotor rotary in the chamber on an axis transverse to the axis of the bore, the rotor having a raised ridge extending along an exterior surface of the rotor corresponding to the parting line of a mold;
- the end formation and closure being formed with cooperative bearing recesses which mate to provide a generally cylindrical bearing for the rotor when the closure mates with the end formation;
- a drive shaft extending through said bore having a forward end in said chamber; and
- a gear on the forward end of the drive shaft mating with a gear on the rotor;
- said cylindric bearing comprising a cylindric surface having a juncture discontinuity thereon formed by mating surfaces of the closure and the recessed end formation, said juncture discontinuity having a segment which is not parallel to the axis of the rotor.

14. A dental prophy angle comprising:
- an elongate hollow body comprising a tubular handle and a tubular extension extending from the handle at one end thereof, the tubular extension having a bore therethrough from the end thereof at the handle to its other end constituting its forward end;
- a chamber at the forward end of the tubular extension; and
- a drive shaft having a longitudinal axis, first and second opposite ends, a first section on one side of a plane extending through the shaft generally transverse to the longitudinal axis, said first section extending from the plane to said first end of the shaft, and a second section on an opposite side of the plane extending from the plane to said second end of the shaft, said first section of the shaft having an outside diameter which does not substantially increase along the first section in a direction from said plane to said first end and said second section of the shaft having an outside diameter which does not substantially increase along the second section in a direction from said plane to said second end whereby the shaft is formed as an integral molded part in a mold the shaft having a parting line ridge corresponding to said plane, said drive shaft being configured for insertion, rear end first, into said bore from the forward end of the tubular extension.

15. The dental prophy angle of claim 14 wherein the outside diameter of the first section of the shaft decreases along the first section in the direction from said plane to said first end and wherein the outside diameter of the second section of the shaft decreases along the second section in the direction from said plane to said second end.

16. A dental prophy angle comprising:
- an elongate hollow body comprising a tubular handle and a tubular extension extending from the handle at one end thereof, the tubular extension having a bore therethrough from the end thereof at the handle to its other end constituting its forward end;
- a chamber at the forward end of the tubular extension;
- a drive shaft having a longitudinal axis, first and second opposite ends, a first section on one side of a plane extending through the shaft generally transverse to the longitudinal axis, said first section extending from the plane to said first end of the shaft, and a second section on an opposite side of the plane extending from the plane to said second end of the shaft, said first section of the shaft having an outside diameter which does not substantially increase alone the first section in a direction from said plane to said first end and said second section of the shaft having an outside diameter which does not substantially increase along the second section in a direction from said plane to said second end whereby the shaft is formed as an integral molded part in a mold having a parting line corresponding to said plane, said drive shaft being configured for insertion, rear end first, into said bore from the forward end of the tubular extension; and
- a raised collar extending circumferentially around the shaft, said collar being adapted to frictionally releasably retain the drive shaft in a first piece of said mold on said one side of said plane when a second piece of said mold on said opposite side of said plane is moved away from said first piece of said mold, said collar having an outside diameter which is sufficiently small so as not to prevent the shaft from being formed as an integral molded part in mold having said parting line corresponding to said plane.

17. A dental prophy angle comprising:
an elongate hollow body comprising a tubular handle and a tubular extension extending from the handle at one end thereof, the tubular extension having a bore therethrough from the end thereof at the handle to its other end constituting its forward end;
a chamber at the forward end of the tubular extension; and
a drive shaft having an elongate shape and a longitudinal axis extending through said bore, which drive shaft is inserted into said bore, rear end first, from the forward end of the tubular extension, and which drive shaft is a molded piece having a mold parting line ridge extending circumferentially of the shaft and not longitudinally of the shaft.

18. The dental prophy angle of claim 17 wherein the drive shaft is formed by a process comprising injecting a fluid plastic precursor material into an elongate mold cavity having a shape corresponding to the drive shaft shape and a longitudinal axis corresponding to the drive shaft longitudinal axis, the elongate mold cavity being defined by a mold having first and second mold pieces such that the longitudinal axis of the mold cavity extends from the first mold piece, through an interface between the first mold piece and the second mold half, and into the second mold piece.

19. The dental prophy angle of claim 18 wherein the longitudinal axis of the mold cavity is perpendicular to the interface between the first and second mold pieces.

20. The dental prophy angle of claim 18 wherein the drive shaft has spaced-apart bearing surfaces.

21. A dental prophy angle comprising:
an elongate hollow body comprising a tubular handle and a tubular extension extending from the handle at one end thereof, the tubular extension having a bore therethrough from the end thereof at the handle to its other end constituting its forward end;
a chamber at the forward end of the tubular extension;
a horizontal drive shaft in said bore having a central longitudinal axis and a drive gear with gear teeth at the forward end of the drive shaft, said drive shaft being configured for insertion, rear end first, into said bore from the forward end of the tubular extension; and
a rotor rotary in the chamber on an axis transverse to the axis of the bore, said rotor comprising a driven gear with gear teeth adapted for engagement with the gear teeth of said drive gear, said rotor having a generally vertical cylindric section extending generally parallel to the rotor axis, said cylindric section being sized for continuous engagement by a flat surface at the forward end of the drive shaft over a substantial area of said flat surface to limit the forward movement of the drive shaft toward the rotor and thus limit the forward force applied to the driven gear by the driving gear.

22. The dental prophy angle of claim 21 wherein said rotor has a reduced diameter clearance section immediately below said vertical cylindric section, said clearance section having an outside diameter smaller than said cylindric section to provide a clearance between the drive shaft and the clearance section when the drive shaft engages said cylindric section of the rotor.

23. The dental prophy angle of claim 22 wherein said vertical cylindric section of the rotor is located adjacent a portion of the drive shaft above said central longitudinal axis, and wherein said clearance section of the rotor is located adjacent a portion of the drive shaft below said central longitudinal axis.

24. The dental prophy angle of claim 21 wherein said cylindric section is sized for engagement by the forward end of the drive shaft over substantially the entire upper half of the drive shaft gear to limit the forward movement of the drive shaft toward the rotor and thus limit the forward force applied to the driven gear by the driving gear.

25. A dental prophy angle comprising:
an elongate hollow body comprising a tubular handle and a tubular extension extending from the handle at one end thereof, the tubular extension having a bore therethrough from the end thereof at the handle to its other end constituting its forward end;
a chamber at the forward end of the tubular extension;
a horizontal drive shaft in said bore having a central longitudinal axis and a drive gear with gear teeth at the forward end of the drive shaft; and
a rotor rotary in the chamber on an axis transverse to the axis of the bore, said rotor comprising a driven gear with gear teeth adapted for engagement with the gear teeth of said drive gear, said rotor having a generally vertical cylindric section extending below the driven gear and generally parallel to the rotor axis, said cylindric section being sized for continuous engagement by a flat surface at the forward end of the drive shaft over a substantial area of said flat surface to limit the forward movement of the drive shaft toward the rotor and thus limit the forward force applied to the driven gear by the driving gear.

26. A dental prophy angle comprising:
an elongate hollow body comprising a tubular handle and a tubular extension extending from the handle at one end thereof, the tubular extension having a bore therethrough from the end thereof at the handle to its other end constituting its forward end, and a chamber at the forward end the tubular extension;
a rotor rotary in the chamber on an axis transverse to the axis of the bore; and
a drive shaft having a longitudinal axis, first and second opposite ends, a first section on one side of a plane extending through the shaft generally transverse to the longitudinal axis, said first section extending from the plane to said first end of the shaft, and a second section on an opposite side of the plane extending from the plane to said second end of the shaft, said first section of the shaft having an outside diameter which does not substantially increase along the first section in a direction from said plane to said first end and said second section of the shaft having an outside diameter which does not substantially increase along the second section in a direction from said plane to said second end whereby the shaft is formed as an integral molded part in a mold having a parting line corresponding to said plane, the drive shaft having two spaced-apart shaft bearing surfaces which contact two spaced-apart bore bearing surfaces inside the tubular extension.

27. The dental prophy angle of claim 26 wherein the tubular extension has an interior taper between said two spaced-apart bore bearing surfaces.

28. A dental prophy angle comprising:
an elongate one-piece hollow body of molded plastic material comprising a tubular handle and a tubular extension extending from the handle at one end thereof;
a bore through the tubular extension from the end thereof at the handle to its other end constituting its forward end, and a chamber at the forward end the tubular extension;
a rotor rotary in the chamber on an axis transverse to the axis of the bore;

a drive shaft extending through said bore; and a gate imperfection on an external surface of the elongate hollow body which is covered over and hidden from view upon securement of the rotor and drive shaft in place, said gate imperfection being remote from bearing surfaces for the rotor and the drive shaft.

29. The prophy angle of claim 28 wherein the gate imperfection is covered over by a component of the prophy angle which assists in securing one of the rotor and drive shaft in place.

30. The prophy angle of claim 28 having a recessed forward end formation at the forward end of the tubular extension defining a forwardly opening recess and a closure for the recess, said closure being configured to cover the gate imperfection upon application of the closure to the forward end formation to close the recess.

31. A dental prophy angle comprising:

an elongate hollow body comprising a tubular handle and a tubular extension extending from the handle at one end thereof, the tubular extension having a bore therethrough from the end thereof at the handle to its other end constituting its forward end;

a chamber at said forward end of the tubular extension;

a rotor rotary in the chamber on an axis transverse to the axis of the bore, said rotor having a lengthwise rotor ridge;

a drive shaft extending through said bore having a forward end in said chamber;

a gear on the forward end of the drive shaft mating with a gear on the rotor;

a generally cylindric rotor bearing for the rotor; and a generally cylindric drive shaft bearing for the drive shaft;

said rotor bearing having a juncture discontinuity thereon formed by mating components of the angle, said juncture discontinuity having a segment which is not parallel to a longitudinal axis of said rotor bearing; and a continuous bearing surface adjacent said juncture discontinuity which supports the drive shaft as it wipes over said juncture discontinuity and thereby reduces impact between said lengthwise ridge in the rotor and said juncture discontinuity.

* * * * *

UNITED STATES PATENT AND TRADEMARK OFFICE
CERTIFICATE OF CORRECTION

PATENT NO. : 6,203,322 B1
DATED : March 20, 2001
INVENTOR(S) : David Kraenzle

It is certified that error appears in the above-identified patent and that said Letters Patent is hereby corrected as shown below:

Column 16, claim 14,
Line 22, "in a mold the shaft" should read -- in a mold, the shaft --.

Column 16, claim 16,
Line 48, "increase alone" should read -- increase along --.

Signed and Sealed this

Eleventh Day of December, 2001

*Attest:*

NICHOLAS P. GODICI
*Attesting Officer*  *Acting Director of the United States Patent and Trademark Office*